United States Patent [19]

Kira et al.

[11] Patent Number: 5,808,256
[45] Date of Patent: Sep. 15, 1998

[54] METHOD OF CONTROLLING A PHOTOREACTION WITH A LASER BEAM

[75] Inventors: Mitsuo Kira, Sendai; Shinya Koshihara, Tokyo; Takashi Miyazawa; Yusaburo Segawa, both of Sendai, all of Japan

[73] Assignee: Rikagaku Kenkyusho, Saitama-ken, Japan

[21] Appl. No.: 787,087

[22] Filed: Jan. 22, 1997

Related U.S. Application Data

[63] Continuation of Ser. No. 352,066, Nov. 30, 1994, abandoned.

[30] Foreign Application Priority Data

Dec. 7, 1993 [JP] Japan .................................. 5-306164

[51] Int. Cl.⁶ .................................................. C07B 61/00
[52] U.S. Cl. .............................. 204/157.15; 204/157.22; 204/157.41; 204/157.61
[58] Field of Search ........................ 204/157.15, 157.22, 204/157.41, 157.61

[56] References Cited

U.S. PATENT DOCUMENTS

| | | | |
|---|---|---|---|
| 4,350,577 | 9/1982 | Heller ................................. | 204/157.22 |
| 4,461,686 | 7/1984 | Tuccio et al. ..................... | 204/157.12 |
| 4,655,890 | 4/1987 | Robinson et al. ................. | 204/157.22 |

OTHER PUBLICATIONS

"Two–Photon Photochromism of a Naphthopyran Derivative",M. Uchida and M. Irie, J. American Chemical Society, vol. 115, No. 14, 1993, 6442–6443.

"Detection and assignment of the 'phantom' photochemical singlet of trans–stilbene by two–proton excitation", Stachelek et al., J. Chem. Phys., vol. 66, No. 10, 15 May 1977, 4541–4543.

Karlov N. K, "Laser Induced Chemical Reactions." *Applied Optics.* vol. 13, No. 2 Feb. 1974, 301–309.

"Detection and Assignment of the Phantom . . . " Stachelek et al, *J. Chem. Phys,* vol. 66, No. 10, 15 May 1977, 4541–4543.

Primary Examiner—Cecilia J. Tsang
Assistant Examiner—C. Delacroix-Muirheid
Attorney, Agent, or Firm—Griffin, Butler Whisenhunt & Szipl, LLP

[57] ABSTRACT

A target is irradiated with a laser beam having an energy of hv/n, where n is an integer, instead of the photon energy hv required for a reaction to proceed using a conventional single-photon excitation method. A desired reaction is selectively induced by the absorption of multiple photons instead of single photons. It is thus possible to induce a photoreaction in which an absorption is carried out in accordance with a selection theory different from that of single-photon absorption, and which is quite different from a photoreaction induced by a single-photon excitation. Namely, a target or reactant is irradiated with a photon energy $hv_2$ having a wavelength integral times longer than that of the photon energy $hv_1$ necessary for a photoreaction to proceed. Photon energy $hv_2$ is either used in place of the photon energy $hv_1$ necessary for a photoreaction, or together with the photon energy $hv_1$, to thereby make the reactant absorb the energy equal to the photon energy $hv_1$. The method is capable of selectively and preferentially inducing a specific photoreaction among various possible, concurrent photoreactions.

16 Claims, 7 Drawing Sheets

| Irrad. Wavelength/nm | Input Power /mJ | Products and Yields / % | |
|---|---|---|---|
| | | 2 | 3 |
| 266 | 11 | 53 | 30 |
| 532 | 160 | 80 | 13 |
| 1064 | 120 | no reaction | |

METHOD OF CONTROLLING A PHOTOREACTION WITH A LASER BEAM

This application is a continuation of Ser. No. 08/352,066, filed Nov. 30, 1994, now abandoned.

FIELD OF THE INVENTION

The invention relates to a method of controlling a photoreaction with a laser beam, and more particularly to a method of controlling the photoexcitation of irradiated substances.

DESCRIPTION OF THE PRIOR ART

A laser beam is, like an electron beam and X-rays, one of the electromagnetic waves. Considering the laser beam to be made up of particles (photons), the energy of light is represented by the photon energy hv which is a product of the frequency v of the light and Planck's constant h. In so-called single-photon excitation, the photon energy hv is supplied by monochromatic light having a frequency v, whereas in so-called multi-photon excitation, the photon energy hv is supplied by monochromatic light having a frequency v/n where n is an integer greater than or equal to two.

The photochemical reactions generated by laser beams have been utilized so far in surface treatment, purification and chemical synthesis. Since the photon energy hv ranging from the ultraviolet spectrum to the vacuum ultraviolet spectrum is larger than the bond energy between atoms, it is possible to induce photo-dissociation and photoreaction of the reactant gas molecules by irradiating them with an ultraviolet laser. Thus, it is possible, by a reaction in which photo-dissociation and photoreaction are induced by irradiating a reactant with the photon energy hv, to achieve a number of desired objectives. These objectives include: the synthesis of chemical compounds such as medicines and other products of chemical synthesis, the synthesis of substances from which optical materials can be manufactured, the control of gas-phase CVD reactions, the micro-machining surface treatment of various materials by using solid-phase photoreactions, the formation of thin films by using laser CVD, and reforming of surface layers such as laser doping.

However, the above photoreactions are generally complex and vary greatly. Hence the control of these reactions is difficult. Accordingly, it has heretofore been difficult to selectively control the synthesis of materials by using the photoreactions, or to control micro-machining surface treatments by using the photochemical processes. In conventional photoreaction methods, only single-photon photoexcitation has been utilized, wherein the photon energy hv is supplied through a monochromatic light having a frequency v. In the single-photon photoreaction, in order to control the photoreaction it is necessary to: (a) control the wavelength of the light, (b) control the temperature, (c) vary the solvent, etc., and/or (d) utilize various sensitizers or quenchers. However, in general, even if the wavelength of the light were to be varied, only a small effect can be obtained. If a plurality of reactions are concurrently carried out, the variation of temperature and solvents, and the use of sensitizers and quenchers generally facilitate all the reactions, and it is therefore impossible to selectively carry out or induce only one of the desired reactions. Thus, in conventional photoreaction methods, problems result by unnecessary reactions being carried out, and unnecessary materials being produced. In addition, if a medium or coexistent material intensely absorbs light, it is difficult for the conventional photoreaction method to induce a photoreaction in a target material in such a medium.

Figure 7A:
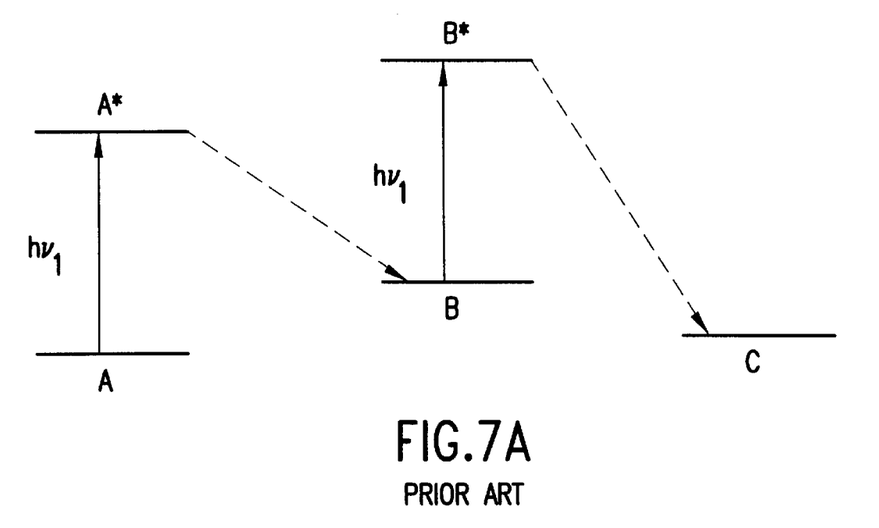
FIG. 7(A) shows a conventional method.
Figure 7B:
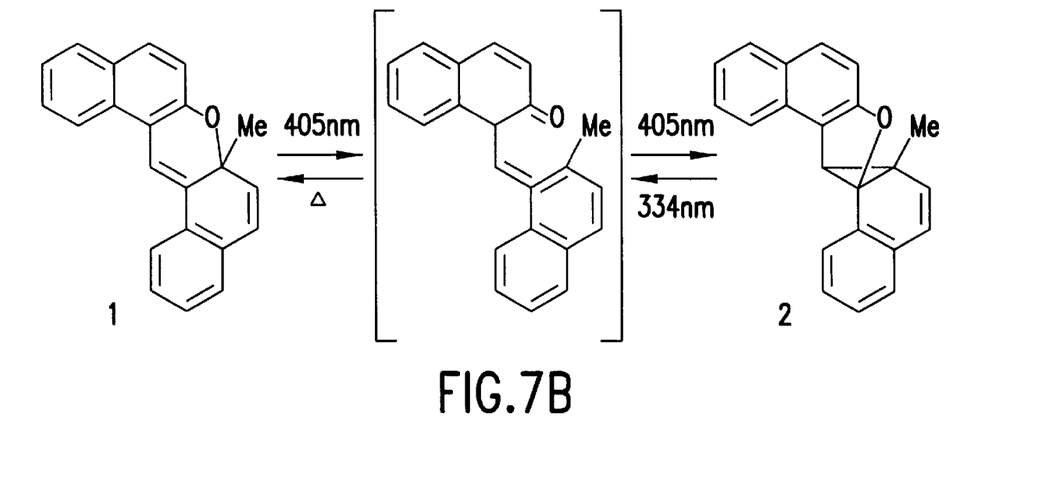
FIG. 7(B) shows a reaction induced by the conventional method.

Research has been conducted in a method of synthesizing a material by successively inducing single-photon photoreactions. FIG. 7(A) shows such a prior art method, and FIG. 7(B) shows an example of a reaction induced by the method. As shown in FIG. 7(A), the method includes the steps of irradiating a reactant A with a photon of energy $hv_1$ to thereby transfer the reactant A into the excited state A* with the result that the reactant A* is transformed into a product B. Product B is thereafter again irradiated with the photon energy $hv_1$ to thereby transfer B into excitation state B* with the result that the product B* is subsequently transformed into a material C (M. Irie and M. Uchida, J. American Chemical Society, 115, 6442, 1993). In FIG. 7(B), the reactant A (indicated with a numeral 1) is a naphthopyran derivative, the material B is an unstable keto form of a naphthopyran derivative, and the material C (indicated with a numeral 2) is a bicyclohexane derivative. However, it is required in this method that the intermediate B have a half-life longer than a certain time, and thus the prior art method never suggests a solution to the problems of unnecessary reactions being carried out and unnecessary materials being synthesized.

The present invention has been made in order to solve the foregoing problems. Namely, it is an object of the present invention to provide a method of controlling a photoreaction with a laser beam, which method is quite different from the conventional method of controlling a photoreaction. The method of the present invention is capable of selectively and preferentially inducing a specific photoreaction among various possible, concurrent photoreactions.

SUMMARY OF THE INVENTION

In accordance with the present invention, there is provided a method of controlling a photoreaction with a laser beam, characterized in that, a reactant, instead of being irradiated with a photon energy $hv_1$ necessary for a photoreaction, is reacted with a photon energy $hv_2$ having a wavelength integral times longer than that the photon energy $hv_1$. There is also provided a method of controlling a photoreaction with a laser beam, characterized in that a reactant is irradiated concurrently with a photon energy $hv_1$ necessary for a photoreaction, and a photon energy $hv_2$ having a wavelength integral times longer than that of the photon energy $hv_1$.

In accordance with a preferred embodiment of the invention, the photon energy $hv_1$ is generated by a Nd:YAG laser which emits a coherent beam of light having a wavelength of 266 nm, and the photon energy $hv_2$ is generated by a Nd:YAG laser which emits a coherent light beam having a wavelength of 532 nm. In accordance with another preferred embodiment of the invention, the target or reactant is one of 2,2-diphenyl-1,1,1,3,3,3-hexamethyltrisilane, cis-stilbene and trans-stilbene.

The present invention is based on a novel discovery that by concurrent multi-photon excitation, wherein a target is irradiated with a photon energy of a multi-photon such as hv/2 and hv/3, instead of photon energy (hv) in accordance with the conventional single-photon excitation method, it is possible to induce a photoreaction in which an absorption is carried out in accordance with a selection theory different from that of the single-photon absorption, and which is quite different from a photoreaction induced by a single-photon. On the basis of the above mentioned discovery, the present invention provides a method of controlling a photoreaction by concurrent multi-photon irradiation which is quite different from the conventional method.

In accordance with the present invention, in place of the photon energy $hv_1$ necessary for a photoreaction, a reactant is irradiated with the photon energy $hv_2$ having a wavelength integral times longer than that of the photon energy $hv_1$, to make the reactant absorb the energy equal to the photon energy $hv_1$ by the simultaneous absorption of multiple photons. It is thereby possible to induce a photoreaction quite different from a photoreaction induced by a single-photon absorption. Thus, it is possible to selectively and preferentially induce a specific photoreaction among a plurality of possible concurrent photoreactions. Furthermore, a reactant can be concurrently irradiated with both the photon energy $hv_1$ necessary for a photoreaction and the photon energy hv2 having a wavelength integral times longer than that of the photon energy $hv_1$, in order to make the reactant absorb the energy $hv_1$ by the simultaneous absorption of multiple photons. It is thereby possible to control the reaction rate of a specific photoreaction among a plurality of possible, concurrent photoreactions.

Further objects, features and advantages of the present invention will become apparent from the Detailed Description of the Preferred Embodiments when considered together with the attached Drawings.

DETAILED DESCRIPTION OF THE PREFERRED EMBODIMENTS

Hereinbelow will be explained preferred embodiments in accordance with the invention with reference to the drawings.

Figure 1A:
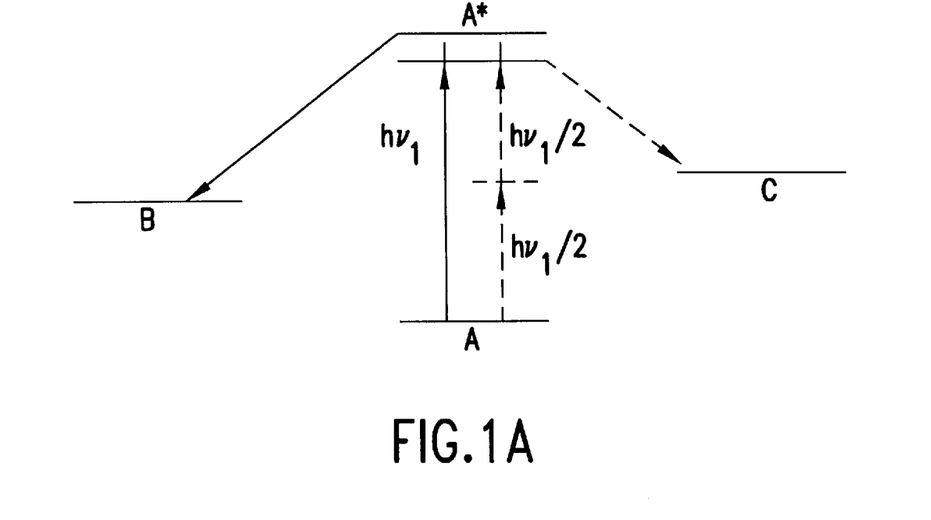
FIG. 1(A) shows a method of controlling a photoreaction with laser beam in accordance with the invention.
Figure 1B:
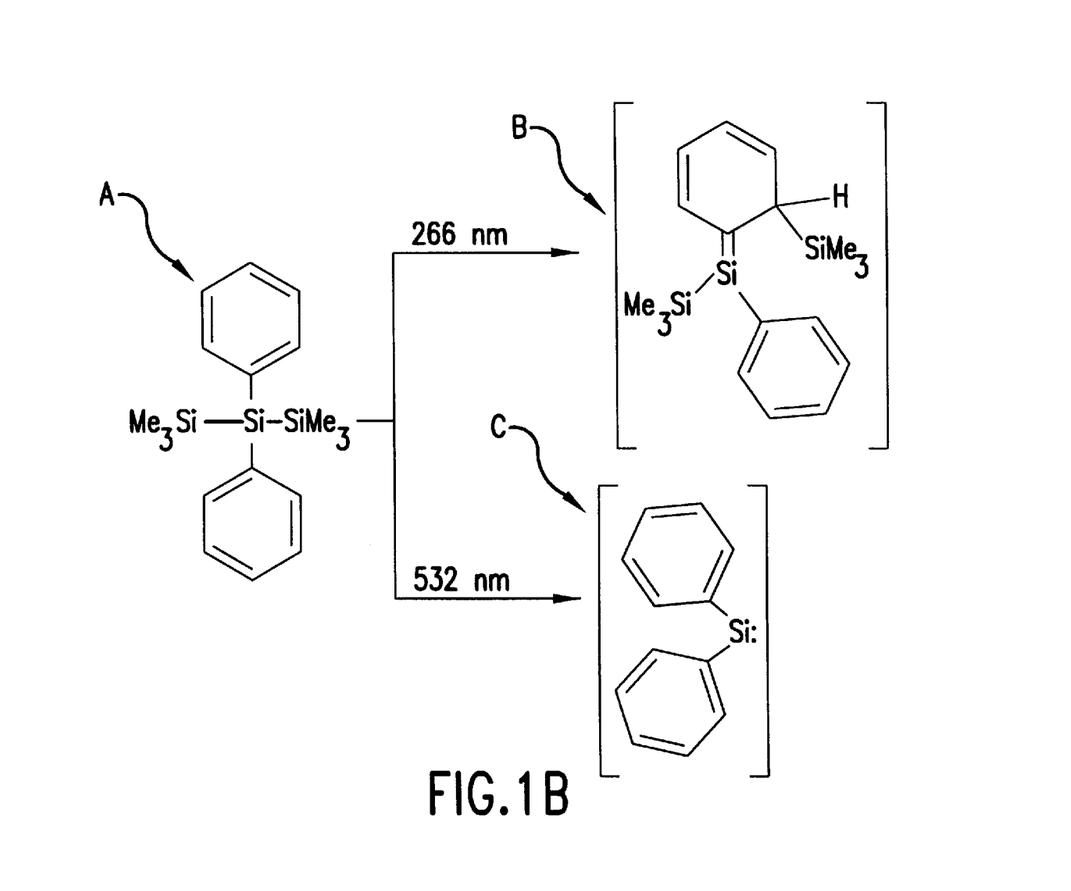
FIG. 1(B) shows an example of a reaction induced by the method.

FIG. 1(A) schematically shows a method of controlling a photoreaction with a laser beam in accordance with the invention, and FIG. 1(B) shows an example of a reaction induced by the method. As shown in FIG. 1(A), in accordance with the invention, a reactant is irradiated with photons of energy $hv_2$ having a wavelength integral times longer than that of the photon energy $hv_1$ required to transfer reactant A to an excited state A*. The reactant A* is transformed into products B and C. The photon energy $hv_2$ is preferably equal to $hv_1/2$ in comparison with the photon energy $hv_1$ required for single-photon excitation. As an alternative thereto, the photon energy $hv_2$ may be equal to a photon energy having a wavelength integral times longer than that of the photon energy $hv_1$, such as $hv_1/3$ and $hv_1/4$. In other words, the same amount of energy is supplied to a reactant by irradiating with a photon energy requiring the simultaneous absorption of multiple photons, such as $hv/2$ and $hv/3$, in place of the photon energy $hv$ necessary for single-photon absorption. The reactant may be concurrently irradiated with both the photon energy $hv_1$ necessary for the photoreaction, and a photon energy $hv_2$ having a wavelength integral times longer than that of the photon energy $hv_1$. In accordance with the invention, as shown in FIG. 1(B), a product including B as a main constituent is produced by inducing a single-photon excitation in the reactant A with light having a wavelength of 266 nm, whereas a product including C as a main constituent is produced by inducing simultaneous multi-photon absorption in the reactant A with light having a wavelength of 532 nm.

Figure 2:
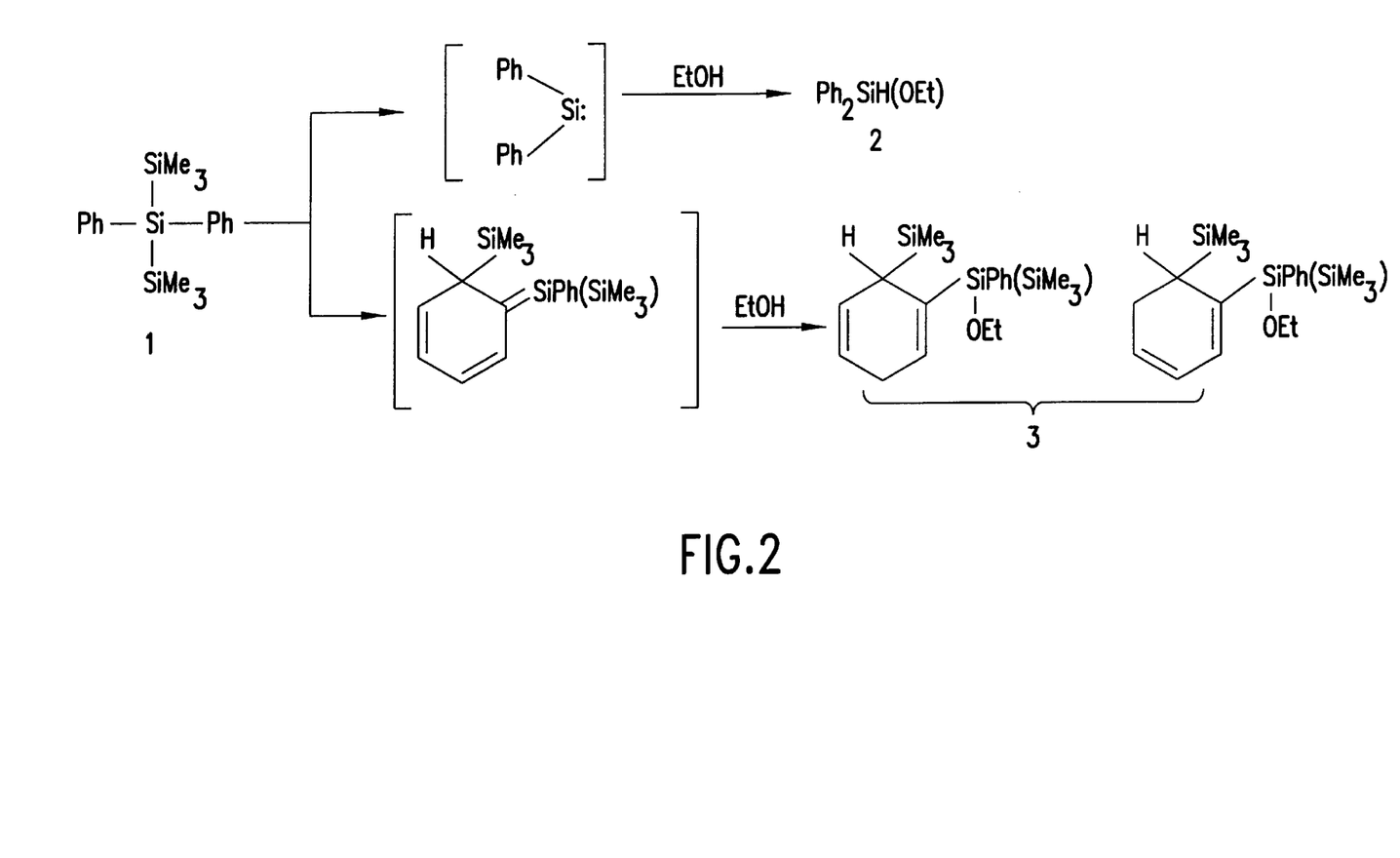
FIG. 2 shows a reaction induced by a first embodiment in accordance with the invention.

FIG. 2 shows a reaction induced by a first embodiment in accordance with the invention. In the embodiment shown in FIG. 2, the reactant A in FIG. 1 is a hexane solution of 2,2-diphenyl-1,1,1,3,3,3-hexamethyltrisilane (indicated by reference numeral 1), the products B and C are silylene to which ethanol is added (indicated by reference numeral 2) and 1,3 transformation reaction product (indicated with a numeral 3), respectively. The photon energy $hv_1$ is an irradiation energy generated by a Nd:YAG laser which emits coherent light having a wavelength of 266 nm, and the photon energy $hv_2$ is generated by a Nd:YAG laser which emits coherent light having a wavelength of 532 nm.

Figure 3:
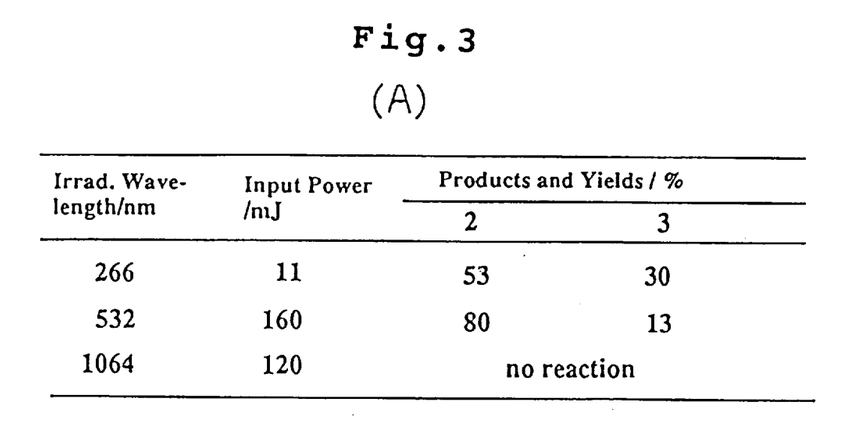
FIG. 3(A) shows the relationship between wavelength of irradiation, power and product yields.
FIG. 3(B) shows the relationship between relative yield of product (2) and time.
FIG. 3(C) shows the relationship between relative yield of product (2) and power.

FIG. 3(A) is a table showing the results of an experiment in which the wavelength and input power of the Nd:YAG laser is varied in the first embodiment. As is apparent from the table of FIG. 3(A), in accordance with a conventional single-photon excitation method, the hexane solution of 2,2-diphenyl-1,1,1,3,3,3-hexamethyltrisilane (product 1) was transformed into silylene having ethanol added thereto (product 2) and the 1,3 transformation reaction product (product 3) with yields of 53% and 30%, respectively, by irradiating with a fourth higher harmonic wave having a wavelength of 266 nm (11 mJ) from a pulsed Nd:YAG laser. In accordance with the concurrent multi-photon excitation method of the present invention, product 1 was irradiated with a second higher harmonic wave having a wavelength of 532 nm (160 mJ) from a pulsed Nd:YAG laser to thereby induce product 1 to absorb the energy equal to the photon energy generated by the fourth higher harmonic wave having 266 nm wavelength, with the result that product 2 and product 3 were obtained in yields of 80% and 13%, respectively. Thus, it is confirmed that the invention can selectively and preferentially induce a photoreaction to produce the product 2.

FIG. 3(B) shows the relationship between the irradiation time indicated along the abscissa and the amount of product 2 (silylene having ethanol added thereto) produced. As shown in FIG. 3(B), the slope relative to the logarithmic axis is approximately 1 (exactly 0.94). This means that production of product 2 is proportional to the irradiation time.

FIG. 3(C) shows the relationship between the input power and the amount product 2 produced. As is apparent from FIG. 3(C), the production yield of product 2 is proportional to approximately the square of the input power, since a slope relative to the logarithmic axes is 2.1. This means that a reaction for producing silylene proceeds through a two-photon excitation state induced by the invention. Thus, the two-photon excitation method in accordance with the invention can selectively induce a reaction for producing silylene shown in FIG. 1.

Figure 4A:
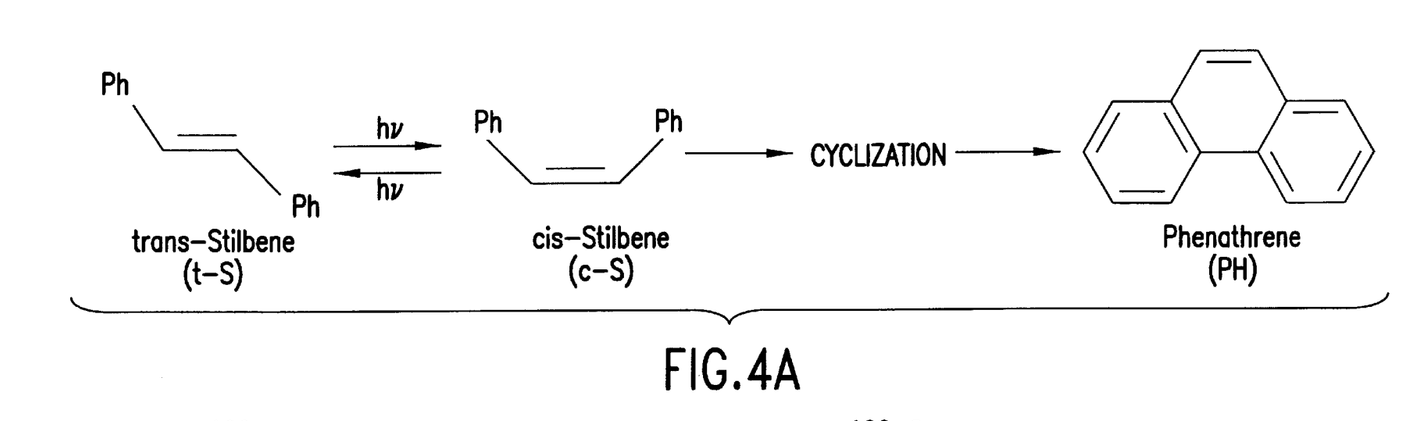
FIG. 4(A) shows a reaction according to a second embodiment in accordance with the invention.
Figure 4B:
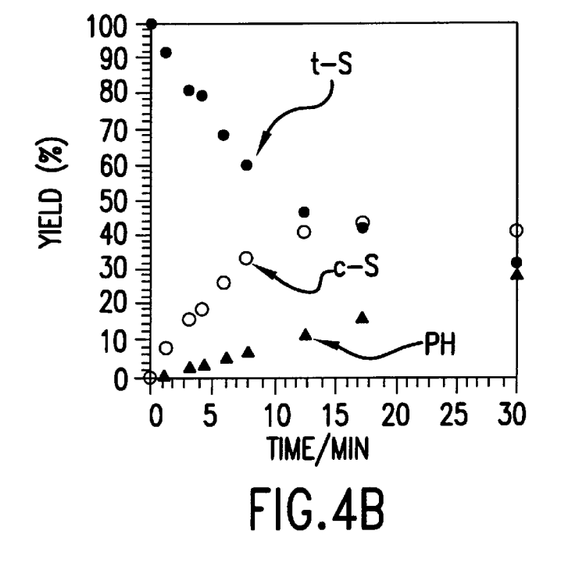
FIGS. 4(B) and 4(C) show yields of a conventional single-photon excitation method.
Figure 4C:
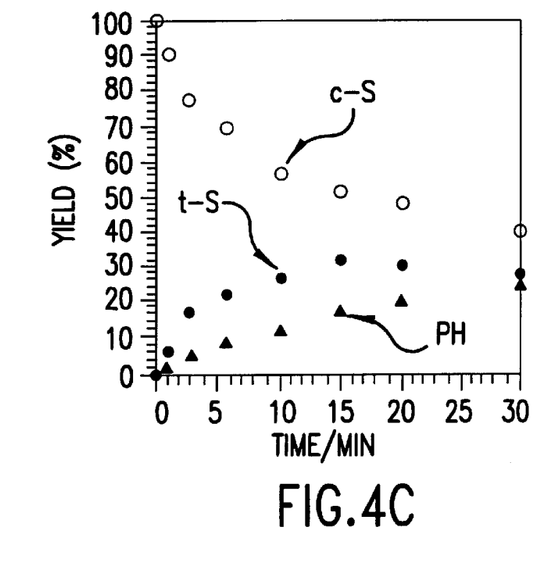

FIG. 4 shows a reaction mechanism (A) of a second embodiment in accordance with the invention, and also shows yields of a conventional single-photon excitation method in (B) and (C). In the second embodiment, trans-stilbene (t-S) and cis-stilbene (c-S) are used as reactants. These reactants are related to one another by a reversible reaction. Namely, the reactant t-S is transformed into a reactant c-S by exciting t-S with a laser beam, and the reactant c-S is transformed into a reactant t-S by exciting c-S with a laser beam. If the reactant c-S is cyclized, phenanthrene (PH) is produced. Phenanthrene (PH) is an undesired by-product of the reaction.

Using a conventional single-photon excitation method, by irradiating trans-stilbene (t-S) with a fourth higher harmonic wave having a wavelength of 266 nm (11 mJ) from a pulsed Nd:YAG laser, cis-stilbene (c-S), trans-stilbene (t-S) and phenanthrene (PH) are obtained in yields of approximately 42%, 28% and 24%, respectively, as shown in FIG. 4(B). On the other hand, as shown in FIG. 4(C), by irradiating cis-stilbene (c-S) with a fourth higher harmonic wave having a wavelength of 266 nm (11 mJ) from a pulsed Nd:YAG laser, cis-stilbene (c-S), trans-stilbene (t-S) and phenanthrene (PH) are obtained in yields of approximately 39%, 27% and 23%, respectively. Thus, it has heretofore been impossible to prevent the production of the undesired reaction product phenanthrene (PH).

Figure 5:
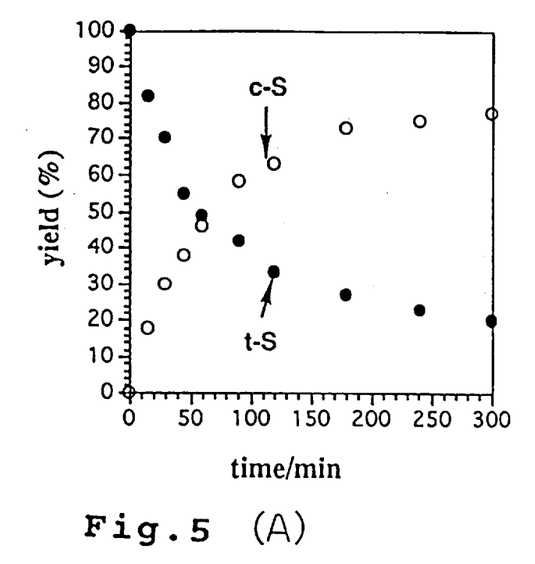
FIGS. 5(A) and 5(B) show the relationship between time and yields in the second embodiment for reactions starting with trans-stilbene and cis-stilbene, respectively.

FIG. 5 shows yields of the simultaneous multi-photon excitation method in accordance with the invention. In the simultaneous multi-photon excitation method, a hexane solution of trans-stilbene (t-S) was irradiated with a second higher harmonic wave having a wavelength of 532 nm (160 mJ) from a pulsed Nd:YAG laser to thereby induce t-S to absorb the energy equal to the photon energy $hv_1$ of the fourth higher harmonic wave having a wavelength of 266 nm by multiple photon absorption. As shown in FIG. 5(A), the solution reached an equilibrium state in approximately 150 minutes. The yields of cis-stilbene (c-S) and trans-stilbene (t-S) were 80% and 16%, respectively, and no phenanthrene PH was produced. Similarly, if cis-stilbene (c-S) was irradiated with a second higher harmonic wave having a wavelength of 532 nm, cis-stilbene (c-S) and trans-stilbene (t-S) were produced in almost the same yields, as shown in FIG. 5(B), without the production of unwanted phenanthrene PH. Thus, it was confirmed that the method according to the present invention can provide only cis-stilbene (c-S) and trans-stilbene (t-S) without producing the undesired product phenanthrene (PH).

Figure 6:
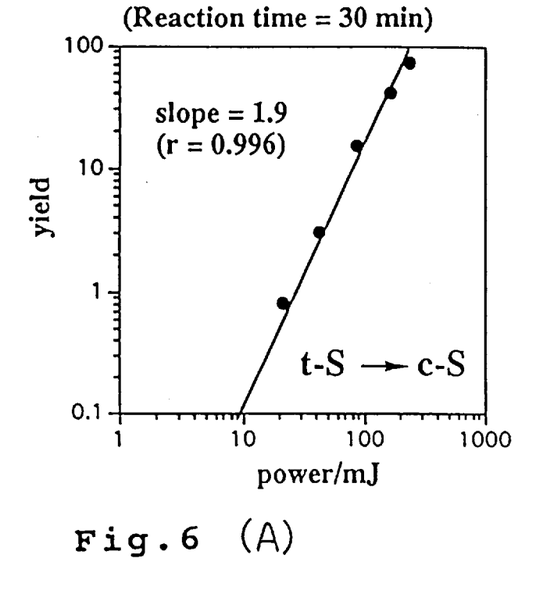
FIGS. 6(A) and 6(B) show the relationship between input power and yields in the second embodiment for reactions starting with trans-stilbene and cis-stilbene, respectively.

FIG. 6 shows the relationship between input power and an isomerization yield in the concurrent multi-photon excitation method in accordance with the invention. As is apparent from FIGS. 6(A) and (B), the production yield of cis-stilbene (c-S) and trans-stilbene (t-S) is in proportion to the approximate square of the input power. This means that a reaction proceeds through a two-photon excitation state, similar to the first embodiment. Thus, the concurrent multi-photon excitation method can produce only cis-stilbene (c-S) and trans-stilbene (t-S) without producing the unwanted phenanthrene (PH) cyclization product.

The present invention is not intended to be limited to the above mentioned embodiments. The present invention is based on a novel discovery that it is possible to induce a specific photoreaction, which is quite different from that induced by a single-photon, by using the above mentioned multi-photon excitation mechanism. In place of the photon energy $hv_1$ induced by a conventional single-photon excitation method, a photoreaction is carried out in accordance with a selection theory which is different from that of single-photon absorption. The present invention can be modified and varied without departing from the scope of the invention.

The present invention makes it possible to control a photoreaction which was difficult to control using a conventional single-photon excitation method. Thus, the invention provides additional new methods for selective synthesis of useful products and micro-processing based on photoreactions. Since it is possible in accordance with the invention to introduce a material into a high energy state by irradiating with light having a relatively long wavelength, there is the additional advantage that photoreaction can be carried which may be impossible to carry out with the conventional method.

Thus, the method of controlling a photoreaction with laser beam in accordance with the invention provides an advantageous effect that only a specific photoreaction can be selectively and preferentially induced among a plurality of possible, concurrent photoreactions, by means of a process quite different from a conventional method for controlling photoreactions.

While the present invention has been illustrated by means of several preferred embodiments, one of ordinary skill in the art will recognize that modification, addition and improvements can be made while remaining within the scope and spirit of the present invention. The scope of the present invention is determined solely by the appended claims.

What is claimed is:

1. A method of controlling a desired photoreaction, comprising the steps of:

irradiating a target with a laser beam having a photon energy $hv_1/n$, wherein n is 2 or greater, and $hv_1$ is an energy necessary to excite the target to a higher electronic state to make the desired reaction proceed to thereby induce an electronic state by multiple photon excitation by the simultaneous absorption of two or more photons, and selectively inducing the desired reaction.

2. A method of controlling a desired photoreaction comprising the steps of concurrently irradiating a target with a first laser beam having a photon energy $hv_1$ necessary to excite the target to a higher electronic state for a desired photoreaction to proceed, and a second laser beam having photon energy $hv_1/n$, wherein n is an integer 2 or greater to thereby induce an excited electronic state by multiple photon excitation by the simultaneous absorption of one or more photons, and selectively inducing the desired reaction.

3. The method as recited in claim 1, wherein said photon energy $hv_1$ is that generated by a Nd:YAG laser which emits coherent light having a wavelength of 266 nm, and said photon energy $hv_1/n$ is that generated by a Nd:YAG laser which emits light having a wavelength of 532 nm.

4. The method as recited in claim 2, wherein said photon energy $hv_1$ is that generated by a Nd:YAG laser which emits coherent light having a wavelength of 266 nm, and said photon energy $hv_1/n$ is that generated by a Nd:YAG laser which emits light having a wavelength of 532 nm.

5. The method as recited in claim 1, wherein said target is 2,2-diphenyl-1,1,1,3,3,3-hexamethyltrisilane.

6. The method as recited in claim 1, wherein said target is cis-stilbene.

7. The method as recited in claim 1, wherein said target is trans-stilbene.

8. The method as recited in claim 2, wherein said target is 2,2-diphenyl-1,1,1,3,3,3-hexamethyltrisilane.

9. The method as recited in claim 2, wherein said target is cis-stilbene.

10. The method as recited in claim 2, wherein said target is trans-stilbene.

11. A method according to claim 1, wherein n is 2.

12. A method according to claim 1, wherein n is 3.

13. A method according to claim 1, wherein n is 4.

14. A method according to claim 1, wherein n is 2.

15. A method according to claim 1, wherein n is 3.

16. A method according to claim 1, wherein n is 4.

* * * * *

UNITED STATES PATENT AND TRADEMARK OFFICE
CERTIFICATE OF CORRECTION

PATENT NO.    : 5,808,256
DATED         : September 15, 1998
INVENTOR(S)   : Kira et al.

It is certified that error appears in the above-identified patent and that said Letters Patent is hereby corrected as shown below:

<u>Column 8,</u>
Lines 6, 7 and 8, "claim 1" should be -- claim 2 --.

Signed and Sealed this

Twenty-fourth Day of June, 2003

JAMES E. ROGAN
*Director of the United States Patent and Trademark Office*